(12) United States Patent
Rabinowitz

(10) Patent No.: US 11,607,510 B2
(45) Date of Patent: Mar. 21, 2023

(54) METHODS AND DEVICES FOR CONTROLLED DRUG VAPORIZATION

(71) Applicant: THE TRUSTEES OF PRINCETON UNIVERSITY, Princeton, NJ (US)

(72) Inventor: Joshua Rabinowitz, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 17/499,151

(22) Filed: Oct. 12, 2021

(65) Prior Publication Data

US 2022/0023551 A1 Jan. 27, 2022

Related U.S. Application Data

(63) Continuation of application No. 16/096,901, filed as application No. PCT/US2017/029908 on Apr. 27, 2017, now Pat. No. 11,154,667.

(60) Provisional application No. 62/458,741, filed on Feb. 14, 2017, provisional application No. 62/329,351, filed on Apr. 29, 2016.

(51) Int. Cl.
| | |
|---|---|
| *A61M 15/00* | (2006.01) |
| *A61M 15/06* | (2006.01) |
| *A61M 16/00* | (2006.01) |
| *A61M 11/04* | (2006.01) |

(52) U.S. Cl.
CPC ........ *A61M 15/0065* (2013.01); *A61M 15/06* (2013.01); *A61M 11/042* (2014.02); *A61M 2016/0024* (2013.01); *A61M 2202/064* (2013.01); *A61M 2205/0238* (2013.01); *A61M 2205/3331* (2013.01); *A61M 2205/3368* (2013.01); *A61M 2205/3653* (2013.01); *A61M 2205/8206* (2013.01)

(58) Field of Classification Search
CPC .... A61M 2016/0024; A61M 2202/064; A61M 15/0065; A61M 15/06; A61M 11/042; A61M 2205/0238; A61M 2205/3331; A61M 2205/3368; A61M 2205/3653; A61M 2205/8206
USPC .......................................................... 131/329
See application file for complete search history.

(56) References Cited

U.S. PATENT DOCUMENTS

| | | | | |
|---|---|---|---|---|
| 2003/0032638 | A1* | 2/2003 | Kim | ..................... A61K 31/404 |
| | | | | 424/46 |
| 2007/0209661 | A1* | 9/2007 | Smyth | ............... A61M 15/0045 |
| | | | | 128/203.15 |
| 2013/0126389 | A1* | 5/2013 | Holakovsky | ........... B65D 83/56 |
| | | | | 206/232 |
| 2013/0276799 | A1* | 10/2013 | Davidson | .......... A61M 15/0003 |
| | | | | 131/273 |
| 2016/0089508 | A1* | 3/2016 | Smith | ............... A61M 15/0085 |
| | | | | 128/202.21 |

* cited by examiner

*Primary Examiner* — Khiem M Nguyen
(74) *Attorney, Agent, or Firm* — J. Clinton Wimbish; Nexsen Pruet, PLLC

(57) ABSTRACT

The present invention an electronic inhaler for the delivery of pharmaceuticals through vaporization.

21 Claims, 6 Drawing Sheets

METHODS AND DEVICES FOR CONTROLLED DRUG VAPORIZATION

CROSS REFERENCE TO RELATED APPLICATIONS

This application is a continuation of U.S. patent application Ser. No. 16/096,901 filed on Oct. 26, 2018, which is a United States National Phase of PCT/US2017/029908 filed on Apr. 27, 2017, which claims the benefit of U.S. Provisional Application No. 62/329,351 filed on Apr. 29, 2016 and U.S. Provisional Application No. 62/458,741 filed on Feb. 14, 2017, each of which is incorporated herein by reference in its entirety.

BACKGROUND OF THE INVENTION

Delivery of pharmaceuticals through inhalation is a rapid process for treating medical conditions because inhaled pharmaceuticals can be absorbed quickly, and can act both locally and systemically. Inhalation is the most rapid way to deliver drugs to the brain, as the substance travels directly to the brain without being diluted by circulation. Inhalation medical devices are also less invasive than other routes of drag administration, such as injection.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention comprises an inhalation device comprising: a) an outer compartment having an airflow pathway therein; b) a cartridge containing a first pharmaceutical, wherein the cartridge is configured to pass a vapor of the first pharmaceutical to the airflow pathway; c) a heating element having a resistance of 0.2-3 Ohm, wherein the heating element is configured to heat the first pharmaceutical, wherein the heating element is configured to be heated by passage of an electrical current; and d) an oral administration port connected to the airflow pathway and configured to pass the vapor of the first pharmaceutical from the airflow pathway to a user's mouth.

DETAILED DESCRIPTION OF THE INVENTION

Figure 1:
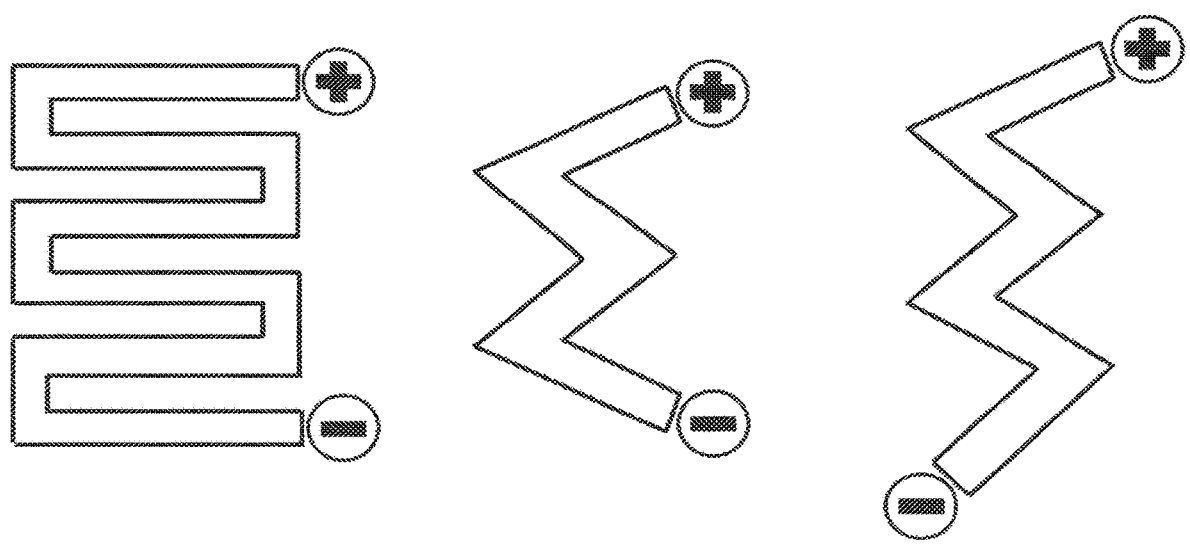
FIG. 1 illustrates examples of the foil heating element.

Electronic inhalation devices deliver chemicals, pharmaceuticals, and other substances to a subject by inhaled vapor. Generally, a personal inhalation device holds a medium that contains a drug and is atomized when a user draws or puffs on the device, thereby creating a vapor containing the drug. The user inhales the vaporized substance.

Inhalation devices provide several advantages as an alternative to smoked tobacco products. Inhaling a vapor containing nicotine can preclude the tar and other harmful effects of traditional tobacco smoke. The vapor dissipates quickly, and reduces the hazards of secondhand smoke. Inhalation devices avoid the fire hazard and environmental problems associated with tobacco smoking because no combustion is involved.

Inhalation devices can deliver uncontrolled and inconsistent dosages, which can raise regulatory issues. The present invention provides rapid delivery of controlled quantities of drags to the lung, and systemic circulation, and the brain. This delivery provides rapid treatment of medical conditions including, for example, pain, breakthrough pain, cancer pain, anxiety, panic attacks, seizures, nausea, vomiting, loss of appetite, and insomnia.

Provided herein are devices and methods for the delivery of pharmaceuticals through heating and vaporization. The device comprises a disposable cartridge that contains a single dose of medicine coated on a heating element in an airway, and a reusable controller that contains a battery, integrated circuit, airflow path, and breath sensor. In the cartridge, the medicine resides as a thin film on the surface of a resistive element or on a thermal conductor in thermal contact with the resistive element. The cartridge and controller physically mate, and are electrically connected, such that, upon activation of the breath sensor, the integrated circuit passes current from the battery to the resistive element in the cartridge. The resistive element heats and vaporizes the pharmaceutical, which cools and condenses in the airflow to form an aerosol suitable for inhalation.

Also provided herein are methods for manufacturing devices for delivery of pharmaceuticals through vaporization.

Inhalation can draw the substance through the mouth, the nose, the pharynx, the trachea, or the lungs of a user. Non-limiting examples of inhaled forms of the substance include a substance in the gaseous state or a suspension of fine particles of liquid, solid, or both within a gas including, for example, aerosols, mists, and fumes.

In some embodiments, a substance can comprise a pharmaceutical compound. In some embodiments, the substance can comprise a therapeutic compound or a non-therapeutic compound. A non-therapeutic compound can refer to a compound that can be used for recreational, experimental, or pre-clinical purposes. Classes of drugs that can be used include, but are not limited to, anesthetics, anticonvulsants, antidepressants, antidiabetic agents, antidotes, antiemetics, antihistamines, anti-infective agents, antineoplastics, antiparkinsonian drags, antirheumatic agents, antipsychotics, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, ophthalmic preparations, osteoporosis preparations, prostaglandins, respiratory agents, sedatives and hypnotics, skin and mucous membrane agents, smoking cessation aids, Tourette's syndrome agents, urinary tract agents, and vertigo agents.

In some embodiments, an anesthetic can be selected from one of the following compounds: ketamine and lidocaine.

In some embodiments, an anticonvulsant can be selected from one of the following classes: GABA analogs, tiagabine, vigabatrin; barbiturates such as pentobarbital; benzodiazepines such as clonazepam; hydantoins such as phenytoin; phenyltriazines such as lamotrigine, miscellaneous anticonvulsants, such as carbamazepine, topiramate, valproic acid, and zonisamide.

In some embodiments, an antidepressant can be selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, venlafaxine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericfamine, clovoxamine, iproniazid, isocarboxazid, moclobemide, phenyhydrazine, phenelzine, selegiline, sibutramine, tranylcypromine, ademetionine, adrafinii, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, escitalopram, tofenacin, trazodone, tryptophan, and zalospirone.

In some embodiments, an antidiabetic agent can be selected from one of the following compounds: pioglitazone, rosiglitazone, and troglitazone.

In some embodiments, an antidote can be selected from one of the following compounds: edrophonium chloride, flumazenil, deferoxamine, nalmefene, naloxone, and naltrexone.

In some embodiments, an antiemetic can be selected from one of the following compounds: alizapride, azasetron, benzquinamide, bromopride, buclizine, chlorpromazine, cinnarizine, clebopride, cyclizine, diphenhydramine, diphenidol, dolasetron, droperidol, granisetron, hyoscine, lorazepam, dronabinol, metoclopramide, metopimazine, ondansetron, perphenazine, promethazine, prochlorperazine, scopolamine, triethylperazine, trifluoperazine, triflupromazine, trimethobenzamide, tropisetron, domperidone, and palonosetron.

In some embodiments, an antihistamine can be selected from one of the following compounds: astemizole, azatadine, brompheniramine, carbinoxamine, cetrizine, chlorpheniramine, cinnarizine, clemastine, cyproheptadine, dexmedetomidine, diphenhydramine, doxylamine, fexofenadine, hydroxyzine, loratidine, promethazine, pyrilamine and terfenidine.

In some embodiments, an anti-infective agent can be selected from one of the following classes: antiviral s such as efavirenz; AIDS adjunct agents such as dapsone; aminoglycosides such as tobramycin; antifungals such as fluconazole; antimalarial agents such as quinine; antituberculosis agents such as ethambutol; β-lactams such as cefinetazole, cefazolin, cephalexin, cefoperazone, cefoxitin, cephacetriie, cephaloglycin, cephaloridine; cephalosporins, such as cephalosporin C, cephalothin; cephamycins such as cephamycin A, cephamycin B, and cephamycin C, cephapirin, cephradine; leprostatics such as clofazimine; penicillins such as ampicillin, amoxicillin, hetacillin, carfeciliin, carindacillin, carbenicillin, amylpenicillin, azidocillin, benzylpenicillin, clometocillin, cloxacillin, cyclacillin, methicillin, nafcillin, 2-pentenyipenicillin, penicillin N, penicillin O, penicillin S, penicillin V, dicloxacillin; diphenicillin; heptylpenicillin; and metampicillin; quinolones such as ciprofloxacin, clinafloxacin, difloxacin, grepafloxacin, norfloxacin, ofloxacine, temafloxacin; tetracyclines such as doxycycline and oxytetracycline; miscellaneous anti-infectives such as linezolide, trimethoprim and sulfamethoxazole.

In some embodiments, an anti-neoplastic agent can be selected from one of the following compounds: droloxifene, tamoxifen, and toremifene.

In some embodiments, an antiparkisonian drug can be selected from one of the following compounds: amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergoiide, piribedii, pramipexole, propentofylline, rasagiline, remacemide, ropinerole, selegiline, spheramine, terguride, entacapone, and toicapone.

In some embodiments, an antirheumatic agent can be selected from one of the following compounds: diclofenac, hydroxychloroquine and methotrexate.

In some embodiments, an antipsychotic can be selected from one of the following compounds: acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, c-hlorprothixene, clocapramine, clomacran, clopenthixol, clospirazine, ciothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipnde, risperidone, sertindoie, spiperone, sulpiride, thioridazine, thiothixene, trifluperidol, triflupromazine, trifluoperazine, ziprasidone, zotepine, and zuclopenthixol.

In some embodiments, an anxiolytic can be selected from one of the following compounds: alprazolam, bromazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloral betaine, enciprazine, flesinoxan, ipsapiraone, lesopitron, loxapine, methaqualone, methprylon, propanoic!, tandospirone, trazadone, zopiclone, and Zolpidem.

In some embodiments, an appetite stimulant can be dronabinol.

In some embodiments, an appetite suppressant can be selected from one of the following compounds: fenfluramine, phentermine, and sibutramine.

In some embodiments, a blood modifier can be selected from one of the following compounds: cilostazol, and dipyridamol.

In some embodiments, a cardiovascular agent can be selected from one of the following compounds: benazepril, captoprii, enalapril, quinapril, ramipril, doxazosin, prazosin, clonidine, labetolol, candesartan, irbesartan, losartan, telmisartan, valsartan, disopyramide, flecanide, mexiletine, procainamide, propafenone, quinidine, tocainide, amiodarone, dofetilide, ibutilide, adenosine, gemfibrozil, lovastatin, acebutalol, atenolol, bisoprolol, esmolol, metoprolol, nadolol, pindolol, propranolol, sotalol, diltiazem, nifedipine, verapamil, spironolactone, bumetanide, ethacrynic acid, furosemide, torsemide, amiloride, triamterene, and metolazone.

In some embodiments, a central nervous system stimulant can be selected from one of the following compounds: amphetamine, brucine, caffeine, dexfenfluramine, dextroamphetamine, ephedrine, fenfluramine, mazindol, methyphenidate, pemoline, phentermine, sibutramine, and modafinil.

In some embodiments, a drug for Alzheimer's disease management can be selected from one of the following compounds: donepezil, galanthamine, and tacrin.

In some embodiments, a drug for cystic fibrosis management can be selected from one of the following compounds: CPX, IBMX, XAC, and analogues, 4-phenylbutyric acid; genistein and analogous isoflavones; and milrinone.

In some embodiments, a diagnostic agent can be selected from one of the following compounds: adenosine and aminohippuric acid.

In some embodiments, a dietary supplement can be selected from one of the following compounds: melatonin and vitamin-E.

In some embodiments, a drug for erectile dysfunction can be selected from one of the following compounds: tadalafil, sildenafil, vardenafil, apomorphine, apomorphine diacetate, phentolamine, and yohimbine.

In some embodiments, a gastrointestinal agent can be selected from one of the following compounds: loperamide, atropine, hyoscyamine, famotidine, lansoprazole, omeprazole, and rebeprazole.

In some embodiments, a hormone can be selected from one of the following compounds: testosterone, estradiol, and cortisone.

In some embodiments, a drug for the treatment of alcoholism can be selected from one of the following compounds: naloxone, naltrexone, and disuifiram.

In some embodiments, a drug for the treatment of addiction can be buprenorphine.

In some embodiments, an immunosuppressive can be selected from one of the following compounds: mycophenolic acid, cyclosporin, azathioprine, tacrolimus, and rapamycin.

In some embodiments, a mast cell stabilizer can be selected from one of the following compounds: cromolyn, pemirolast, and nedocromil.

In some embodiments, a drag for migraine headache can be selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diitiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

In some embodiments, a motion sickness product can be selected from one of the following compounds: diphenhydramine, promethazine, and scopolamine.

In some embodiments, a drug for multiple sclerosis management can be selected from one of the following compounds; bencyclane, methylprednisolone, mitoxantrone, and prednisolone.

In some embodiments, a muscle relaxant can be selected from one of the following compounds: baclofen, chlorzoxazone, cyclobenzaprine, methocarbamol, orphenadrine, quinine, and tizanidine.

In some embodiments, a nonsteroidal anti-inflammatory can be selected from one of the following compounds: aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, eiopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and vaklecoxib.

In some embodiments, an opioid can be selected from one of the following compounds: alfentanil, allylprodine, alphaprodine, anileridine, benzyl morphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

In some embodiments, another analgesic can be selected from one of the following compounds: apazone, benzpiperylon, benzydramine, caffeine, clonixin, ethoheptazine, flupirtine, nefopam, orphenadrine, propacetamol, and propoxyphene.

In some embodiments, an opthalmic preparation can be selected from one of the following compounds: ketotifen and betaxolol.

In some embodiments, an osteoporosis preparation can be selected from one of the following compounds: alendronate, estradiol, estropitate, risedronate and raloxifene.

In some embodiments, a prostaglandin can be selected from one of the following compounds: epoprostanol, dinoprostone, misoprostol, and alprostadil.

In some embodiments, a respiratory agent can be selected from one of the following compounds: albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, and pirfenidone In some embodiments, a sedative and hypnotic can be selected from one of the following compounds: butalbital, chlordiazepoxide, diazepam, estazolam, flunitrazepam, flurazepam, lorazepam, midazolam, temazepam, triazolam, zaleplon, Zolpidem, and zopiclone.

In some embodiments, a skin and mucous membrane agent can be selected from one of the following compounds: isotretinoin, bergapten and methoxsalen.

In some embodiments, a smoking cessation aid can be selected from one of the following compounds: nicotine and varenicline.

In some embodiments, a Tourette's syndrome agent can be pimozide.

In some embodiments, a urinary tract agent can be selected from one of the following compounds: tolteridine, darifenicin, propantheline bromide, and oxybutynin.

In some embodiments, a vertigo agent can be selected from one of the following compounds: betahistine and meclizine.

In general, a suitable drug can have properties that make them acceptable candidates for use with the devices and methods herein described. For example, the drug compound can be one that is, or can be made to be, vaporizable. In some embodiments, the drug is a heat-stable drug. Exemplary drugs include acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chiordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester. ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrme, oxycodone, paroxetine, pergolide, phenytoin, pindolol, piribedil, pramipexole, procainamide, prochloperazine, propafenone, propranolol, pyril amine, quetiapine, quinidine, rizatriptan, ropinirole, sertraline, selegiline, sildenafil, spironolactone, tacrine, tadalafil, terbutaline, testosterone, thalidomide, theophylline, tocainide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tolterodine, tramadol, tranylcypromine, trimipramine maieate, valdecoxib, vardenafil, verapamil, zoimitriptan, Zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatnptan, pyrilamine maleate, scopolamine, triamcinolone acetonide, and pharmaceutically acceptable analogs and equivalents thereof.

Non-limiting examples of pharmaceutical compounds include fluticasone propionate, clonidine, triazolam, albuterol, ciclesonide, fentanyl, terbutaline, flumazenil, triamcinolone acetonide, flunisolide, ropinirole, alprazolam, buprenorphine, hyoscyamine, atropine, pramipexoie, bumetanide, flunitrazepam, oxymorphone, colchicine, apomorphine HCl, granisetron, pergolide, nicotine, loperamide, azatadine, naratriptan, clemastine, benztropine, ibutilide, butorphanol, fluphenazine, estradiol-17-heptanoate, zoimitriptan, metaproterenol, scopolamine, diazepam, tolterodine, estazoiam, haloperidol, carbinoxamine, estradiol, hydroniorphone, bromazepam, perphenazine, midazolam, methadone, frovatnptan, eletriptan, testosterone, melatonin, galanthamine, cyproheptadine, bropheniramine, and chlorpheniramine. In certain embodiments, the compound is chosen from alprazolam, buprenorphine, clonindine, fentanyl, midazolam, pramipexole, ropinirole, and triazolam. In some embodiments, the compound is chosen from a compound for the treatment of pain. In some embodiments, the compound for the treatment of pain is fentanyl.

In some embodiments, the pharmaceutical delivered by the inhaler is an opioid agonist or a partial opioid agonist, a benzodiazepine, a cannabinoid agonist, or partial agonist. Non-limiting examples of opioid agonists include fentanyl, sufentanil, buprenorphine, hydromorphone, morphine, oxycodone, tramadol, methadone, hydrocodone, oxycodone, meperidine, oxymorphone, tapentadol, propoxyphene, remifentanil, nutorphanol, alfentanil, and levorphanol. Non-limiting examples of benzodiazepines include alprazolam, triazolam, and midazolam. Non-limiting examples of cannabinoids include tetrahydrocannabinol (THC) and cannabidiol (CBD).

In some embodiments, drugs can be formulated as the free base or free acid form to facilitate vaporization. A drug can be formulated as a prodrug or a drug precursor, which forms the active drug substance upon heating or upon metabolism. For example, tetrahydrocannabinolic acid (THCA) is more stable than THC, and THCA forms THC upon heating and vaporization. Esters of carboxylic acids are more volatile than the associated free acids, and can vaporize more efficiently. These esters can metabolize in the body into the free acids.

In some embodiments, the dosage of the medication provided by the device is about 25 about 50 about 100 about 200 about 250 µm, about 500 or about 1000 µg in a single inhalation. In some embodiments, the thickness of the drug coating is about 1 µm, about 2 µm, about 3 µm, about 4 µm, about 8 µm, about 12 µm, about 15 µm, or about 20 µm. In some embodiments, the heating of the heating element is sufficient to vaporize essentially all or most of the drug coating, for example, at least 90%, at least 95%, at least 98%, or at least 99%, such that the emitted dose from the device is determined by the thickness of the coating multiplied by the coated surface area (SA): dose (µg)=SA (mm3) *thickness (µm)*density (mg/mm3). In some embodiments, the heating element is a foil. For example, a dose of 100 µg of fentanyl can be administered using a surface area of 20 mm' achieved as a 1 mm×20 mm stainless steel foil coated on a single side, at a thickness of 5 µm. The drug can be fully vaporized within about 0.2 s, about 0.4 s, about 0.6 s, about 0.8 s, about 1 s, or about 1.5 s of activation of the breath sensor.

In some embodiments, a cartridge contains only one foil. An advantage of having a cartridge containing only one foil is that using one foil removes the possibility of cross-contamination between foils during either storage or dosing. In addition, the cartridge can be packaged as required to maintain purity and performance (for example, within a polymer and/or metal pouch, including as appropriate barrier materials such as aluminum, polyethylene terephthalate, and barex), and removed from the packaging only at the time that the foil will be used, obviating concerns about stability of the foil after the removal of the foil from the packaging. In some embodiments, a cartridge contains more than one foil. If each foil is designed to deliver one dose of medication, then the drug vaporized during activation of a first foil to deliver a first dose of medication can potentially deposit onto another foil. Subsequent activation of the second foil can result in delivery of a dose that is greater than the intended dose, and can be a safety and regulatory concern. Moreover, repeated vaporization of the drug can result in degradation products that would not otherwise occur in a device containing only one foil. In some embodiments, the geometry and airflow are optimized to avoid excessive re-deposition of the vaporized drug onto other foils.

In some embodiments, a cartridge contains only one foil to lessen the likelihood of overdose, to ensure repeated dose reproducibility, to simplify product testing to meet regulatory requirements, to obviate concerns about the stability of additional foils after use of one or more foils within a cartridge, and/or other reasons. In some embodiments, a cartridge contains more than one foil. A cartridge containing more than one foil can heat at different times and can, in the case of simultaneous heating of multiple files or cross-contamination between foils, deliver a dose that is greater than the prescribed dose.

To achieve drug vaporization, the temperature of the drug coating can be raised through a heating element. The heating element can increase the temperature substantially above room temperature of the surface to which the drug coating is in thermal contact. For example, the temperature of the surface can increase to about 100° C., about 150° C., about 200° C., about 250° C., about 300° C., about 350° C., about 400° C., about 450° C., or about 500° C. For a drug that is prone to thermal degradation, the surface temperature can be kept below about 400° C., 450° C., about 500° C., about 550° C., or about 600° C. to avoid the release of undesirable byproducts or degradation. Vaporization of drug from the surface results in evaporative cooling, which helps control the surface temperature until the drug is fully or partially vaporized. Proper heating can be accomplished by an appropriate pairing of battery, heating element, and controller electronics.

In some embodiments, the battery can be a lithium ion, lithium ion polymer, lead-acid, nickel cadmium, or a nickel metal hydride battery. The battery can produce a voltage in the range of about 3 V to about 4 V. In some embodiments, the operating voltage of the battery is about 3 V, about 3.1 V, about 3.2 V, about 3.3 V, about 3.4 V, about 3.5 V, about 3.6 V, about 3.7 V, about 3.8 V, about 3.9 V, or about 4 V. In some embodiments, the electrical resistance of the heating element is in the range of about 1-3 Ohm. In some embodiments, the electrical resistance of the heating element is in the range of about 1.4-2.8 Ohm. In some embodiments, the electrical resistance of the heating element is in the range of about 0.2-1.0 Ohm. In some embodiments, the electrical resistance of the heating element is about 0.2 Ohm, about 0.3 Ohm, about 0.4 Ohm, about 0.5 Ohm, about 0.75 Ohm, about 1 Ohm, about 1.2 Ohm, about 1.5 Ohm, about 2 Ohm, about 2.5 Ohm, about 3 Ohm, about 4 Ohm, about 5 Ohm, about 7.5 Ohm, or about 10 Ohm. In some embodiments, the controller can employ pulse width modulation to pass current intermittently through, and heat, the foil.

In some embodiments of a pulse sequence, the controller can initially deliver longer or more frequent pulses, and thereafter, deliver shorter or less frequent pulses to achieve rapid initial heating followed by less rapid subsequent heating to avoid overheating of the drug or the device. In some embodiments, the controller can deliver an average power output of greater than 50% or 75% of the maximal output (given the batter}—and circuit resistance, Pmax=V2/R) over a first duration, and can deliver an average power part of less than 50% or 75% of the maximal output over a second duration. In some embodiments, the first duration is at least 0.1 s and no greater than 2 s. In some embodiments, the first duration is about 0.1, about 0.2, about 0.3, about 0.5, about 0.7, about 1, about 1.5, or about 2 s. In some embodiments, the second duration begins immediately at the end of the first duration and continues until termination of heating. In some embodiments, heating turns off when the breath sensor detects the end of inhalation. In some embodiments, heating turns off after a predetermined duration. In some embodiments, the predetermined duration is chosen to be about 0.1 s, about 0.2 s, about 0.5 s, or about 1 s longer than the time required to fully vaporize the drug on the foil when the device is used at the coolest relevant environmental temperature (i.e., the bottom end of the temperature range recommended on the packaging for use of the product).

In some embodiments, the device includes a closed-loop sensor to monitor the temperature of the heating element and adjust the electrical flow accordingly. In some embodiments, the duration of the pulses is determined in part by the voltage of the battery, such that when the battery voltage is lower, the pulses are longer or more frequent, and when the battery voltage is higher, the pulses are shorter or less frequent. The overall effect is a consistent heating mechanism resistant to small variations in the battery voltage as may occur with shelf-life storage or repeated use of the battery.

The device can be made of a variety of materials and have a variety of shapes. In some embodiments, the exterior of the device is made of a medical grade polymer.

The heating element of the device can be made of a variety of materials and have a variety of shapes, while achieving: (i) a suitable electrical resistance to provide efficient heating, (ii) a suitable thermal mass suitable for effective heating by the battery, (iii) a suitable surface area for drug vaporization, and (iv) surface chemistry suitable for drug adherence and to avoid surface-catalyzed drug degradation during either shelf-life storage or the heating and vaporization process. Non-limiting examples of materials that can serve directly as both electrical resistors and supports for the drug vaporization include nichrome and stainless steel.

The electrical resistance of the heating element is determined by both the material and the geometry. For example, for the 1 mm×20 mm stainless steel foil described above, with electrical connections at the distal ends (i.e. 20 mm apart), using an alloy of stainless steel with resistance of 10e"6 Ohm and a stainless steel foil thickness of 0.0005" (0.012 mm), the resistance is 1.6 Ohm. Power output is given by V2/R, resulting, at an operating voltage of 3.5 V in a power output of 7.7 W. The mass of the 1 mm×20 mm×0.012 mm stainless steel foil is 1.92 mg, which, at a heat capacity of 0.5 J/gK, is suitable for heating the foil by 400° C. with 0.38 J, i.e. over 50 ms at 7.7 W. Slower and more controlled heating can occur by delivering the 0.38 J over 100 ms through on-and-off pulses, followed by continued heating over the next 1 s at a reduced rate due to a schedule of off periods with relatively briefer on pulses.

Another example of geometry and material is a nichrome wire of length 40 mm and a diameter of 0.18 mm. Such a wire has a resistance of about 1.6 Ohm, a surface area of about 22 mm2, and a mass of 8 mg, resulting in a requirement for 1.6 J of energy to heat the wire by 400° C. At 3.6 V, such heating can be achieved over 200 ms in the absence of pulse width modulation.

In some embodiments, the thickness of the stainless steel heating element is from about 0.02 mm to about 0.03 mm, from about 0.02 mm to about 0.04 mm, from about 0.02 mm to about 0.06 mm, from about 0.02 mm to about 0.08, from about 0.02 mm to about 0.10 mm, from about 0.02 mm to about 0.12 mm, from about 0.02 mm to about 0.16 mm, or from about 0.02 mm to about 0.2 mm. In some embodiments, the thickness of the stainless steel heating element is about 0.01 mm, about 0.02 mm, about 0.03 mm, about 0.04 mm, about 0.05 mm, about 0.06 mm, about 0.07 mm, about 0.08 mm, about 0.09 mm, about 0.10 mm, about 0.11 mm, about 0.12 mm, about 0.13 mm, about 0.14 mm, about 0.15 mm, about 0.16 mm, about 0.17 mm, about 0.18 mm, about 0.19 mm or, about 0.20 mm.

The shape of the heating element can enhance the mechanical stability of the heating element and thus stability, reproducibility, and performance of device. The shape of the heating element can contribute to uniform heating of the surface of the heating element by uniform heating of replicate heating foils and uniform heating across the heating surface. In some embodiments, the device can achieve a temperature within about 5 K, within about 10 K, within about 15 K, within about 20 K, within about 25 K, within about 30 K, within about 40 K, or within about 50 K of a target temperature on greater than about 50%, greater than about 75%, greater than about 90%, greater than about 95%, or greater than about 98% of the heating surface. The target temperature can be about 100° C., about 150° C., about 200° C., about 250° C., about 300° C., about 350° C., about 375° C., about 400° C., about 450° C., or about 500° C. In some embodiments, there are no detectable hotspots (e.g. greater than about 30 K, greater than about 50 K, greater than about 75 K, or greater than about 100K over the target temperature) based on thermal imaging. In some embodiments, there no detectable cold spots (e.g. greater than about 30 K, greater than about 50 K, greater than about 75 K, or greater than about 100K below the target temperature) based on thermal imaging. Similarly, the device can maintain temperature consistency heating foils, such that the temperature varies by less than about 2%, less than about 5%, or less than about 10%, less than about 5 K, less than about 10 K, less than about 20 K, less than about 25 K, less than about 30 K, or less than about 40 K across batches of 5, 10, 20, 50, 100, or more foils.

Figure 2:
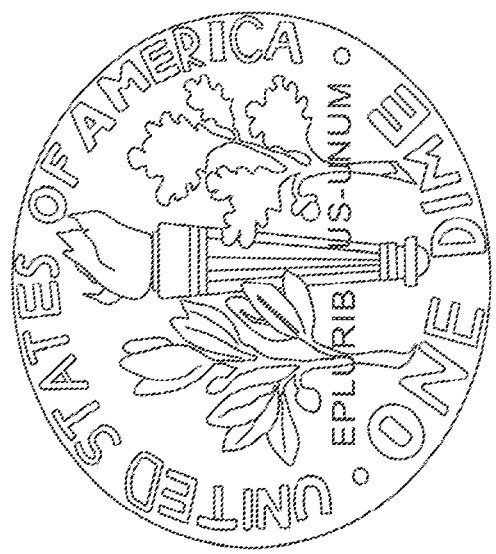
FIG. 2 illustrates examples of a serpentine-shaped foil heating element.
Figure 2:
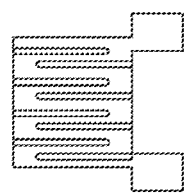
Figure 2:
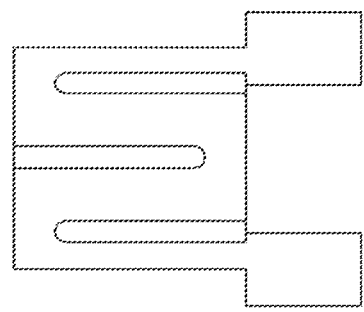
Figure 3:
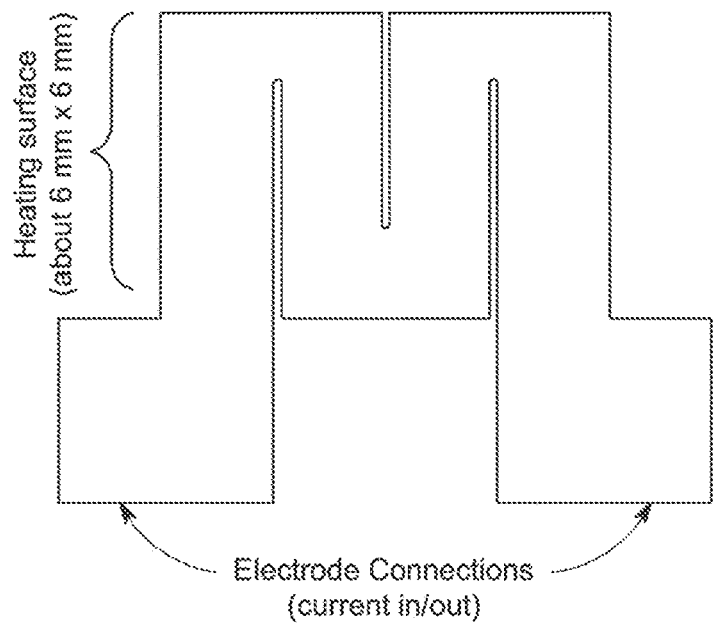
FIG. 3 illustrates an example of a heating foil attached to a holder for connecting to an electrical and/or a mechanical connection.
Figure 3:
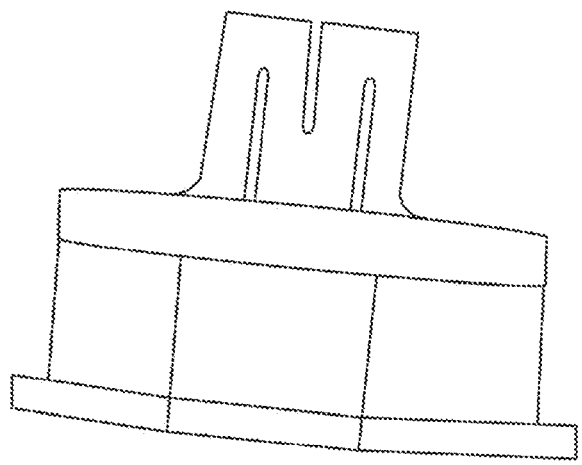

In some embodiments, the heating element can be nonlinear. The heating element can be shaped like a serpentine pattern like a "U" or a zigzag pattern like an "M". The shape of the heating element can vary by the number of lines that make up the serpentine pattern. For example, multiple connected lines on the heating element can improve the mechanical stability, electrical stability, and temperature consistency of the device. For example, the heating element can be a serpentine shape or a zigzag pattern. The shape of the heating element can have 1, 2, 3, 4, 5, 6, 7, 8, 9, 10, or more connected lines arranged in a serpentine or zigzag pattern. In some embodiments, the heating element can be shaped as shown in FIG. 1-3. The connected lines on the heating element can be separated by gaps of varying angles and distances. The angle between the connected lines can be from about 1 degree to about 180 degrees. In some embodiments, the angles can be 90 degrees, as illustrated in FIGS. 2 and 3. In some embodiments, the heating element consists of extremely narrow gaps so that from a distance, the heating element appears solid without gaps. The width of the gaps can be about 0.1 mm, about 0.15 mm, about 0.2 mm, about 0.25 mm, about 0.3 mm, about 0.35 mm, about 0.4 mm, about 0.45 mm, about 0.5 mm, about 0.6 mm, about 0.7 mm, about 0.8 mm, about 0.9 mm, or about 1 mm. The small gaps between the connected lines of the serpentine or zigzag path can induce efficient electrical flow. The small, intervening gaps can allow air flow to function as an electrical insulator by forcing electrical flow to follow the serpentine electrical path. This electrical flow can allow generation of a resistance that is required for effective heating.

FIG. 1 illustrates examples of the foil heating element. The first foil (left) has a serpentine pattern with six connected lines arranged in the serpentine pattern. The middle and right foils have a zigzag pattern with differing numbers of lines arranged in the zigzag pattern. When the heating element is connected to an electrical circuit, the electron current can flow from the negative terminal to the positive terminal.

FIG. 2 illustrates examples of a serpentine-shaped foil heating element. The heating element can range in sizes that are comparable to the size of a dime with a diameter of about 17 mm. In some embodiments, the longest dimension of the foil heating element is less than about 10 mm, less than about 15 mm, less than about 20 mm, or less than about 25 mm. The larger heating element (left) has four connected lines arranged in a serpentine pattern. The heating element (right) has six connected lines arranged in a serpentine pattern. FIG. 3 illustrates an example of a heating element that includes a square or rectangular-shaped heating surface and two electrode connections stemming from the bottom of the heating surface (top). The electrode connections that connect the electrically-resistive heating element to a battery can be made of the same material and about the same thickness as the heating element. For example, the electrode connections can be made of stainless steel. In some embodiments, the width of the electrode connections can be greater than the width of the electrical path. Electrical resistance can scale as width of the electrical connectors. Accordingly, the width of the electrode connections can reduce the electrical resistance of the connection and decrease the heating of the connection, while increasing heating of the foil heating element.

In some embodiments, the area of the heating surface can be greater than about 50%, greater than about 75%, greater than about 90%, or greater than about 95% of the entire heating element. In some embodiments, the width of the gaps between the lines of the heating element (the electrical path) can be less than about 1×, less than about 0.5×, less than about 0.25×, or less than about 0.125× the width of the electrical path. In some embodiments, the heating surface is about 6 mm by about 6 mm. The bottom panel illustrates the heating foil attached to an inert thermally-resistant support (holder) that simultaneously allows for the electrical connections and mechanically holds the foil in place, cantilevered in the air.

To deter misuse or excessive use of a drug, the invention can include lockout features that prevent repeated dosing within pre-determined time intervals. Such lockout features can be implemented without requiring each disposable cartridge to have distinguishing features, to be used in any particular order, or have electronic controls. Instead, the reusable controller can record each usage through a timer and can allow only a certain number of uses per pre-determined time interval. For example, the controller can allow use of a maximum of 1 dose per hour. Alternately, the dosage limitation can involve multiple different time intervals, for example, 1 dose per 30 minutes and no more than 2 doses per every 4 hours. In some embodiments, the controller can recognize a code, such as a bar code or magnetic code, on the disposable cartridges, and would only heat and vaporize such cartridges, detering an inappropriate application of the controller to other cartridges not prescribed to the patient. In some embodiments, the controller can recognize the individual patient, for example, based on a fingerprint, or a passcode.

To deter misuse of a drug in the disposable cartridge, the device can encompass an antagonist of the drug. An antagonist blocks the activity of a drug. For example, an opioid antagonist blocks the activity of an agonist opioid by binding to the opioid receptors. However, the antagonist does not cause an opioid effect. Non-limiting examples of opioid antagonists include naltrexone, naloxone, nalmefene, and samidorphan. Non-limiting examples of benzodiazepine antagonists include flumazenil.

In some embodiments, the portion of the cartridge containing the antagonist is not exposed to the heating element, and vaporization of the drug does not co-vaporize the antagonist. In some embodiments, an antagonist of the drug is contained in a heat-resistant compartment of the cartridge. Tampering with the device to extract the drug, and circumvent the control features, can also extract the antagonist. The antagonist can then mix with the drag and render the drug ineffective for abuse.

Figure 4:
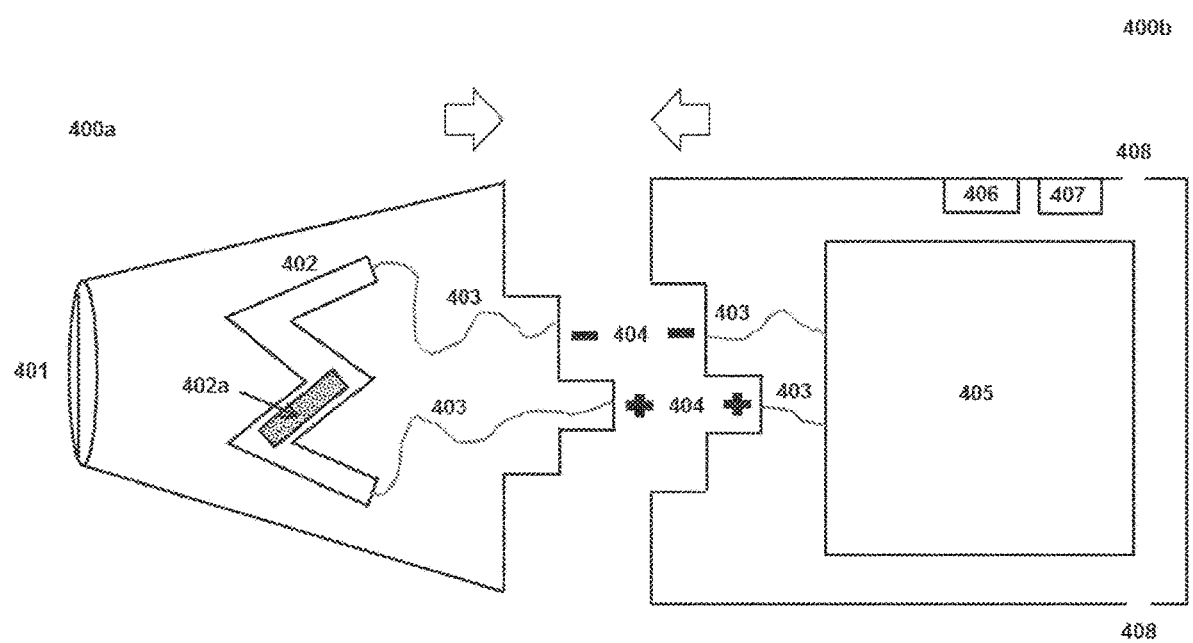
FIG. 4 illustrates an embodiment of the device.

FIG. 4 illustrates an embodiment of the device. The device comprises of a cartridge 400a and a controller 400b, which can be mechanically and electrically connected together for operation of the device. The controller 400b can mate with a single-dose, one-puff, disposable cartridge 400a.

The cartridge 400a contains a mouthpiece 401 and a heating element 402 containing the drug 402a. The heating element can be a drug-coated foil as shown in FIG. 4. In some embodiments, the heating element 402 contains multiple connected lines arranged in a serpentine shape or a zigzag shape. In some embodiments, the width of the exterior lines is thinner than the width of the interior lines. The shape of the heating element can pack substantial surface area into a small heating element with mechanical strength and high electrical resistance. In contrast, if the same serpentine or zigzag line was extended to be a straight line, the mechanical strength would be compromised. Whereas if the shape was filled rather than serpentine or zigzag, the electrical resistance may be less likely to be high enough to effectively heat the foil without excessive risk of shorting or of overheating the battery. In some embodiments, electrical connectors are located near to each other (thereby decreasing the required length of the wires 403 in FIG. 4), on the same edge of the two-dimensional surface of the heating element 402 as shown in the left and middle example of FIG. 1. The controller 400b contains a battery 405, an integrated circuit chip 406, a pressure sensor 407, and air inlets 408.

The cartridge 400a and the controller 400b are mechanically connected by a male/female-shaped connection 404 in a manner that forms an electrical circuit between the cartridge 400a and the controller 400b. Electrical currents pass from the controller 400b to the cartridge 400a through wires 403 connected to the male/female connection 404. The electrical connector 404 joins two lengths of wire 403 that create an electrical circuit between the battery 405 in the controller 400b and the heating element 402 in the cartridge 400a. The wires can be made of various materials including, for example, lead, copper, aluminum, and an alloy thereof.

The air inlets of the controller 400b connect to the airway of the cartridge 400a, and thereby, connect to the mouthpiece 401. To operate the device, the cartridge and the controller are mechanically connected via connection 404 to create an electrical circuit between the battery 405 and the heating element 402. A user can draw or inhale from the mouthpiece 401 to initiate heating of the drug-coated foil 402 and subsequent vaporization of the drug 402a. The controller 400b contains a pressure sensor 407 that can sense inhalation when the device is in use. The pressure sensor 407 senses a pressure change resulting from an inhalation by the user from the mouthpiece 401 and initiates heating of the device. Alternatively, flow or convective cooling can be detected to indicate inhalation. In some embodiments, once inhalation is sensed, the device goes through a full heating cycle irrespective of continued user inhalation. In other embodiments, after inhalation is complete, the pressure sensor 407 can detect the pressure change and powers off heating of the device. The air inlets 408 on the controller 400b allow air to pass from the controller 400b to the airway of cartridge 400a and thereby to the mouthpiece 401 and the user.

Figure 5:
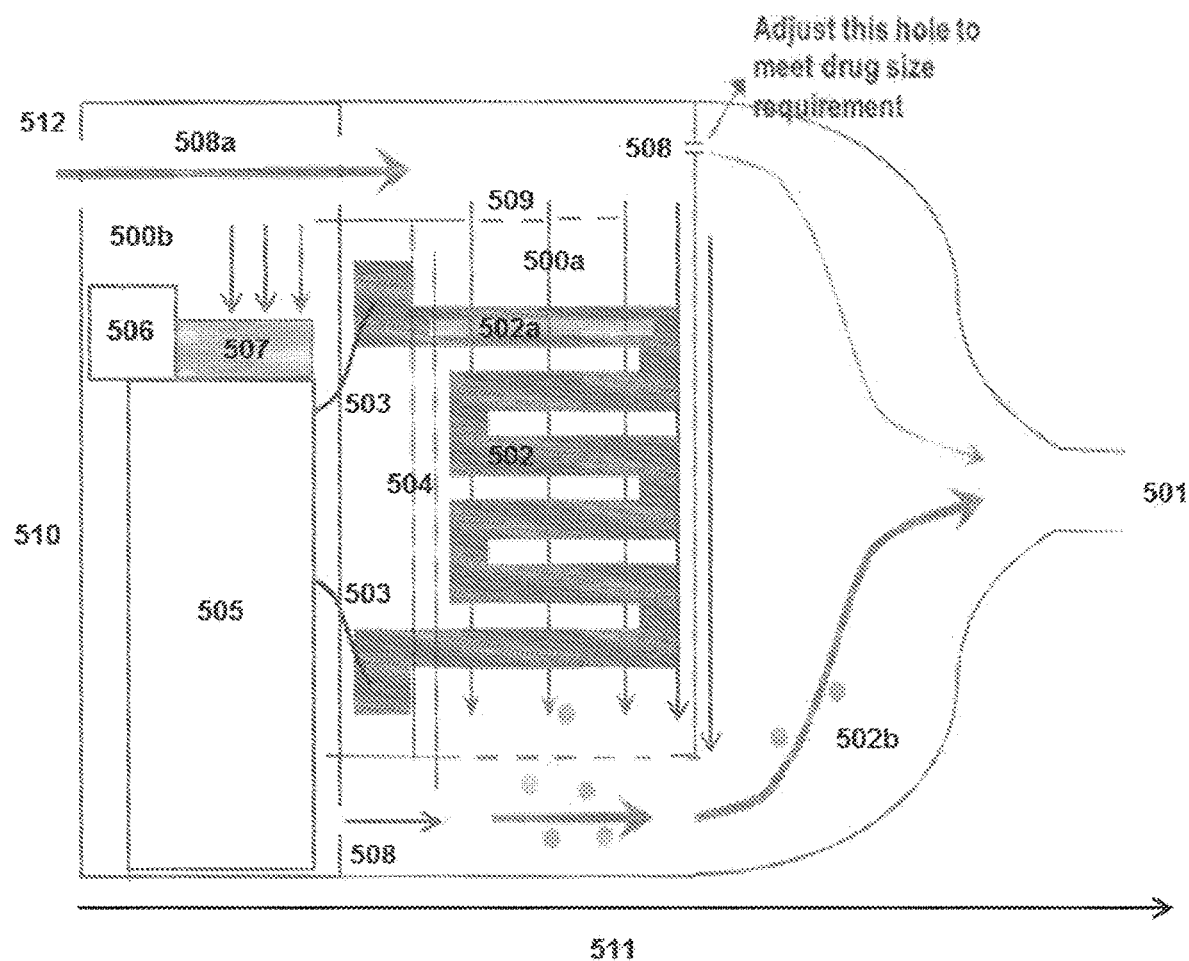
FIG. 5 illustrates an embodiment of the device.

FIG. 5 illustrates an embodiment of the device. The cartridge 500a contains a drug-coated foil heating element 502, The layer of drug 502a is coated on the surface of the heating element 502. The drug 502a can cover a part of or almost the entirety of the foil heating element 502 with margins that are sufficient to avoid overflowing of the drug at the edge of the foil during the coating process. The margin can be at least about 0.02 mm, at least about 0.05 mm, at least about 0.1 mm, or at least about 0.2 mm. The foil heating element is held by one or more thermally-inert support structures 504 that secure the foil within the device through physical interaction with its ends, which are in electrical contact with the wires 503. Alternatively, the wires can be in electrical contact with electrical conductive elements within the support, which are in turn in contact with the foil. The support functions to prevent contact between the foil and the exterior of the airway, holding the parts of the foil that are not in contact with the support suspended in air. In some embodiments, the serpentine or zigzag aspect of the foil is held cantilevered in air by the support as shown in FIG. 3. In some embodiments, the support 504 comprises or consists essentially of ceramic. In some embodiments, the support is not electrically conductive. In some embodiments, the support comprises or consists essentially of metal. In some embodiments, the majority of the support is not electrically conductive and the support comprises metal that facilitates electrical conduction between the wires 503 and the heated foil 502.

The controller 500b is mechanically and electrically connected to the cartridge 500a. The controller 500b contains a breath sensor 507 in electronic communication with an integrated circuit chip 506 that controls the voltage and current and a battery 505. The electrical chip 506 can also control lockout features that prevent repeated dosing within predetermined time intervals or overdosing. The battery 505 is connected to the electrical circuit through wires 503 and provides electricity to heat to the heating element 502. The exterior of the controller 500b contains one or more air inlets 512 that allow air 508a to activate the breath sensor 507 and to pass from the controller into the cartridge 500a. The controller element 500b of the device is reusable and the cartridge 500a can be disposable.

User inhalation draws air 508a through the device. Air 508a flows into the device and activates the breath sensor 507. The breath sensor senses the air movement or pressure change and actuates the passage of electric current from the battery 505 to heat the foil 502. Air flows from the controller 500b into the cartridge 500a, via a continuous airway which is formed by mating of the controller 500b and cartridge 500a. Air then passes, optionally through one or more openings, holes, or slits 509, across the heated foil 502. The location of slits 509 can be chosen to direct air across the heated foil either roughly parallel to or, as shown in FIG. 5, roughly perpendicular to the device axis 511 defined by the position of the mouthpiece 501 relative to the rear of the assembled mated device 510, In embodiments where the airflow over the foil is roughly perpendicular to the device axis 511, the air flow can be either roughly in plane with the heated foil surface 502 as shown in FIG. 5 or perpendicular to the surface. In certain embodiments, airflow from below to above the coated heated surface 502 decreases degradation of the drug 502*a* during its heating and vaporization. As the heated foil 502 heats the drug 502*a*, the drug 502*a* vaporizes and condenses in the incoming air 508*a* into an aerosol 502*b* that is suitable for deep lung inflation. In some embodiments, limiting the airflow over the drug 502*a* is desirable so as to increase the particle size of the aerosol. Limiting the airflow can be achieved by providing a bypass air path 508, where the drag can pass from the air intake to the mouthpiece 501 without passing over the drug 502*a*. The geometry of this air bypass 508 can be modulated to control the fraction of air that passes over the drug 502*a*, e.g., in the design shown in FIG. 5, by modulating the size of the hole 508.

Figure 6:
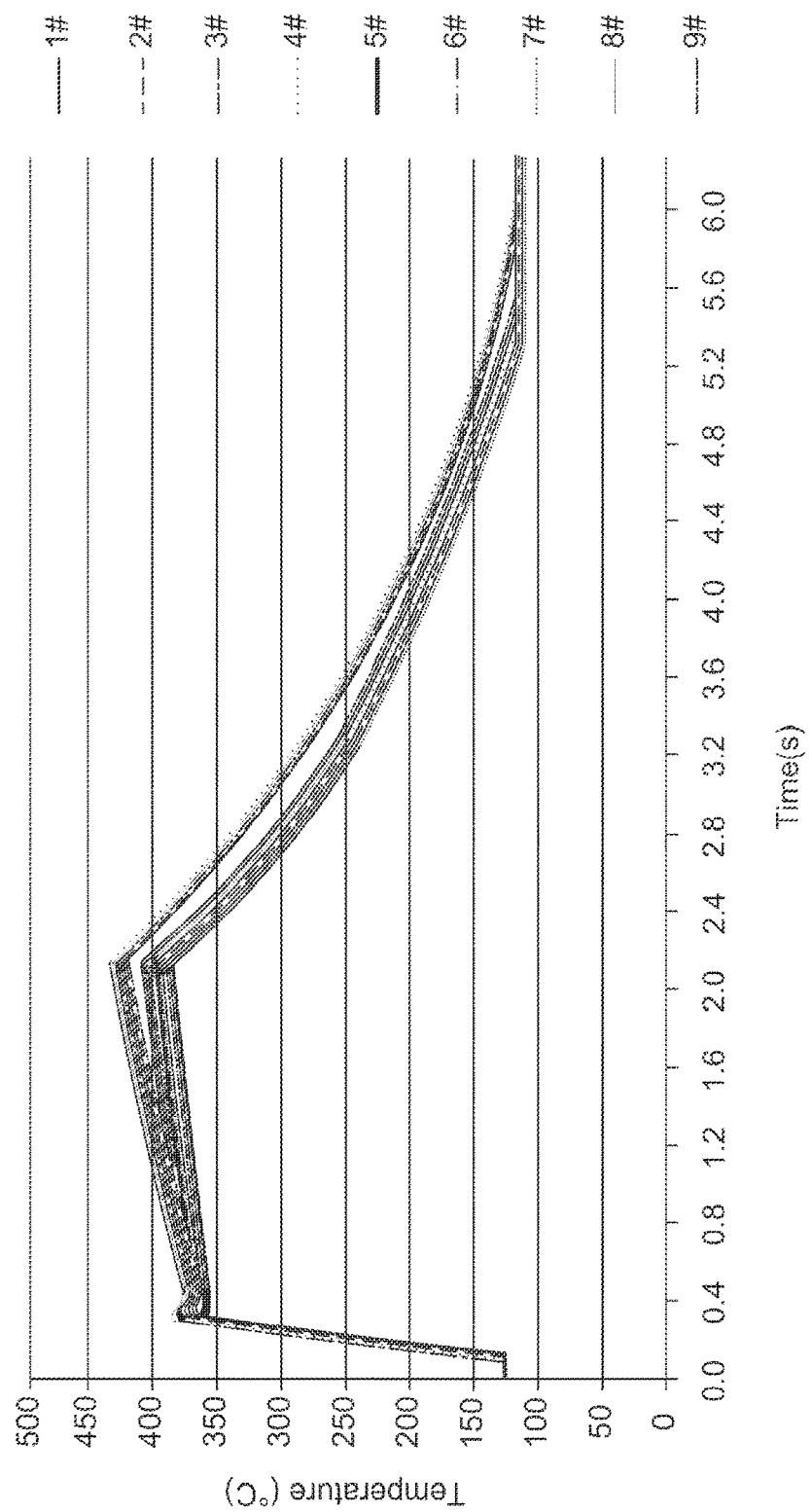
FIG. 6 illustrates the rate of heating of the heating element using thermal imaging.

FIG. 6 illustrates the rate of heating of a heating element using infrared thermal imaging. The temperature of the heating element increased from about 0° C. to about 130° C. in about 0.12 seconds and increased from about 130° C. to about 370° C. in about 0.17 seconds. Together, the temperature of the heating element increased from about 0° C. to about 370° C. in about 0.29 seconds. The highest temperatures recorded were from about 380° C. to about 430° C. No temperature data were obtained below 130° C. because the infrared detection limit was from about 130° C. to about 900° C.

Reproducible delivery to the subject can depend on the aerosol particle size emitted from the device. Particle size is determined by the extent of mixing of the vaporized drug with air. More mixing results in smaller particle size, and less mixing with larger particle size. The particle size of the aerosol can depend on the heating rate and air flow over the drug. The faster the rate of heating, the larger the size of the aerosol particles. The faster the air flow, the smaller the size of the aerosol particles. In some embodiments, the particle size or mean particle size of a population of particles of an aerosol has a mass median aerodynamic diameter of about 0.8 µm, about 1 µm, about 2 µm, about 2.5 µm, about 3 µm, or about 4 µm. In some embodiments, the airway of the device includes a multiplicity of air passages that direct the proper amount of airflow over the vaporizing drug. In some embodiments, the device includes one or more air flow control valves that control the airflow over the vaporizing drug and consistently achieve the desired particle size.

Consistency of the coating can ensure dosage uniformity for the subject, and compliance with regulatory requirements for dose consistency. In some embodiments, the dose loaded is controlled within about 10%, about 5%, about 3%, or about 2% of a prescribed dose through a dip-coating or spray-coating process. The loaded dose can be within about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of a prescribed dose, Another feature of the manufacturing process is compliance with pharmaceutical good manufacturing practice (GMP). GMP provides a system for ensuring that products are consistently produced and controlled according to quality standards to minimize the risks involved in any pharmaceutical production that cannot be eliminated through testing the final product. In some embodiments, the manufacturing process involves assembly of component parts of the controller and/or disposable cartridge in a factory that does not fully conform to pharmaceutical GMP, followed by final assembly in a pharmaceutical GMP environment. For example, the breath sensor, battery, integrated circuit, or airway housing of the controller can be manufactured in one environment, and optionally connected into larger subassemblies, which undergo final assembly and/or testing in a pharmaceutical GMP environment.

Similarly, the airway housing, electrical connections to the controller, or electrical connections to the heating element of the disposable cartridge, or the heating element, can be manufactured in one environment, and optionally connected into larger subassemblies, while the drug coating and final assembly are conducted in a pharmaceutical GMP environment.

The invention claimed is:

1. An inhalation device comprising:
a controller; and
a cartridge comprising an airway and a mouthpiece, the cartridge containing a non-linear heating element disposed within the airway comprising a plurality of connected lines and gaps separating the lines, wherein the non-linear heating element has a heating surface greater than 75% of the non-linear heating element; and
wherein the controller is configured to heat the non-linear heating element via an electrical current to pass a vapor of a compound into the airway.

2. The inhalation device of claim 1, wherein the non-linear heating element is secured within the cartridge by a thermally inert support structure.

3. The inhalation device of claim 1, wherein the non-linear heating element is a foil.

4. The inhalation device of claim 1, wherein the non-linear heating element is a wire.

5. The inhalation device of claim 1, wherein the heating element has a resistance of 0.2-3 Ohm.

6. The inhalation device of claim 1, wherein the heating element has a resistance of up to 10 Ohm.

7. The inhalation device of claim 1, wherein the controller is configured to heat the non-linear heating element via pulse width modulation.

8. The inhalation device of claim 1, wherein the controller is configured to deliver a power output of greater than 50% to the non-linear heating element over a first time period and a power output of less than 50% to the non-linear heating element over a second time period.

9. The inhalation device of claim 1, wherein the non-linear heating element is formed from at least one of stainless steel and nichrome.

10. The inhalation device of claim 1, wherein the non-linear heating element has a thickness from 0.01 mm to 0.20 mm.

11. The inhalation device of claim 1, wherein the surface of the non-linear heating element is uniformly heated.

12. The inhalation device of claim 1, wherein the connected lines of the non-linear heating element are separated by angular gaps having an angle up to 180 degrees.

13. The inhalation device of claim 1, wherein the connected lines of the non-linear heating element are separated by gaps having a width from 0.1 mm to 1 mm.

14. The inhalation device of claim 1, wherein the non-linear heating element comprises a heating surface and at least two electrode connections, the compound coated on a portion of the heating surface, and the electrode connections configured to connect the non-linear heating element to a battery of the controller.

15. The inhalation device of claim 1, further comprising a timer, wherein the timer is configured to disable the passage of current to the non-linear heating element based on a schedule of use.

16. The inhalation device of claim 1, wherein the compound is coated onto the heating element at a thickness of about 1 µm to about 20 µm.

17. The inhalation device of claim 1, wherein the heating of the heating element is sufficient to vaporize at least 90% of the compound.

18. The inhalation device of claim 1, wherein the compound is a respiratory agent.

19. The inhalation device of claim 18, wherein the respiratory agent is selected from the group consisting of ciclesonide, fluticasone propionate, and combinations thereof.

20. The inhalation device of claim 1 further comprising a controller for recording usage of the inhalation device.

21. The inhalation device of claim 20, wherein the controller is operable to lockout use of the inhalation device.

* * * * *